United States Patent [19]

Ayer et al.

[11] 4,444,689

[45] Apr. 24, 1984

[54] 17α-ACYLOXY-5β-CORTICOIDS AND 17α-ACYLOXY-5α-CORTICOIDS

[75] Inventors: Donald E. Ayer; Carl A. Schlagel, both of Kalamazoo, Mich.

[73] Assignee: The Upjohn Company, Kalamazoo, Mich.

[21] Appl. No.: 298,984

[22] Filed: Sep. 3, 1981

Related U.S. Application Data

[62] Division of Ser. No. 117,401, Jan. 31, 1980, Pat. No. 4,318,853.

[51] Int. Cl.³ .............................................. C07J 5/00
[52] U.S. Cl. ...................... 260/397.45; 260/239.55 R; 260/239.55 D
[58] Field of Search ................................... 260/397.45

[56] References Cited

U.S. PATENT DOCUMENTS 4,336,200 6/1982 Ayer et al. ..................... 260/397.45

OTHER PUBLICATIONS

Chemical Abstracts, vol. 94, 1981 Pars. 103680s.

Primary Examiner—Elbert L. Roberts
Attorney, Agent, or Firm—Bruce Stein

[57] ABSTRACT

17α-Acyloxy-5β-pregnanes (I) and 17α-acyloxy-5α-pregnanes (IV) have an excellent activity split providing high topical anti-inflammatory activity with very low systemic side effects.

15 Claims, No Drawings

17α-ACYLOXY-5β-CORTICOIDS AND 17α-ACYLOXY-5α-CORTICOIDS

This is a division of application Ser. No. 117,401, filed Jan. 31, 1980 now U.S. Pat. No. 4,318,853.

The present invention relates to 5α and 5β- 17α-acyloxy corticoids which are useful as topical anti-inflammatory agents for which the essential material constituting a disclosure thereof is incorporated by reference here from U.S. patent application Ser. No. 117,401, filed Jan. 31, 1980, now U.S. Pat. No. 4,318,853.

We claim:

1. A 5β-steroid of the formula

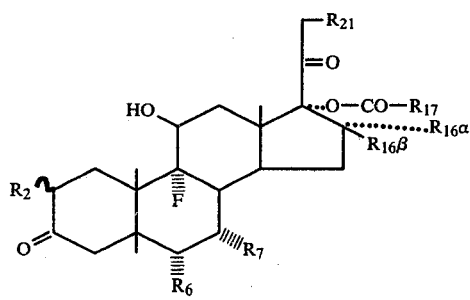

where
- $R_2$ is a hydrogen, fluorine or chlorine atom or methyl group;
- $R_6$ is a hydrogen, fluorine or chlorine atom or methyl group;
- $R_7$ is a hydrogen, fluorine or chlorine atom;
- $R_9$ is a hydrogen, fluorine or chlorine atom;
- $R_{11}$ is a chlorine or oxygen atom or hydroxyl group; when $R_{11}$ is a chlorine atom or hydroxyl group the --- between $R_{11}$ and $C_{11}$ is a single bond in the β configuration and when $R_{11}$ is an oxygen atom the --- between $R_{11}$ and $C_{11}$ is a double bond;
- $R_{16\alpha}$ is a hydrogen, fluorine or chlorine atom or methyl group;
- $R_{16\beta}$ is a hydrogen atom or methyl group with the proviso that one of $R_{16\alpha}$ or $R_{16\beta}$ is a hydrogen atom;
- $R_{17}$ is alkyl of 1 through 6 carbon atoms, phenyl, p-methylphenyl, p-carboxyphenyl or p-carboalkoxyphenyl;
- $R_{21}$ is a hydrogen, fluorine, chlorine or bromine atom or a —$OR_{21\alpha}$ or —$OSO_2CH_3$ group;
- $R_{21\alpha}$ is a hydrogen atom, —$COR_{21\beta}$ or —$PO(OH)_2$ and pharmaceutically acceptable salts thereof;
- $R_{21\beta}$ is alkyl of 1 through 6 carbon atoms, phenyl, p-methylphenyl, or p-carboxyphenyl, p-carboalkoxyphenyl, —$CH_2CH_2COOH$ and pharmaceutically acceptable salts thereof;
- ---- is a single or double bond; and
- ~ indicates the attached group can be in either the α or β configuration.

2. A compound according to claim 1 where $R_2$ is a hydrogen atom or methyl group.

3. A compound according to claim 2 where $R_2$ is a hydrogen atom.

4. A compound according to claim 1 where $R_6$ is a hydrogen or fluorine atom or methyl group.

5. A compound according to claim 4 where $R_6$ is a hydrogen atom.

6. A compound according to claim 1 where $R_7$ is a hydrogen or chlorine atom.

7. A compound according to claim 6 where $R_7$ is a hydrogen atom.

8. A compound according to claim 1 where $R_{16\alpha}$ is a hydrogen atom or methyl group.

9. A compound according to claim 1 where $R_{16\beta}$ is a hydrogen atom or methyl group.

10. A compound according to claim 9 where $R_{16\beta}$ is a methyl group.

11. A compound according to claim 1 where $R_{17}$ is alkyl of 1 thru 5 carbon atoms, phenyl, or paramethylphenyl.

12. A compound according to claim 11 where $R_{17}$ is alkyl of 1 thru 4 carbon atoms or phenyl.

13. A compound according to claim 1 where $R_{21}$ is a hydrogen, fluorine, or chlorine atom or a —$OR_{21\alpha}$ group where $R_{21\alpha}$ is defined in the specification.

14. A compound according to claim 13 where $R_{21}$ is a hydrogen or chlorine atom or —$OR_{21\alpha}$ group where $R_{21\alpha}$ is —$COR_{21\beta}$ where $R_{21\beta}$ is defined in the specification.

15. A compound according to claim 1 which is 21-chloro-9α-fluoro-11β,17α-dihydroxy-16β-methyl-5β-pregnane-3,20-dione 17-propionate.

* * * * *